United States Patent [19]

Zaffaroni

[11] 3,996,934

[45] * Dec. 14, 1976

[54] MEDICAL BANDAGE

[75] Inventor: Alejandro Zaffaroni, Atherton, Calif.

[73] Assignee: Alza Corporation, Palo Alto, Calif.

[ * ] Notice: The portion of the term of this patent subsequent to July 29, 1992, has been disclaimed.

[22] Filed: Aug. 9, 1971

[21] Appl. No.: 169,975

[52] U.S. Cl. .............................. 128/268; 128/260; 128/130

[51] Int. Cl.² .......................................... A61F 7/02

[58] Field of Search .......... 128/260, 268, 130, 156, 128/296

[56] References Cited
UNITED STATES PATENTS

| | | | |
|---|---|---|---|
| 1,280,149 | 10/1918 | Breck et al. | 128/268 UX |
| 2,501,544 | 3/1950 | Shrontz | 128/268 |
| 3,053,255 | 9/1962 | Meyer | 128/268 |
| 3,249,109 | 5/1966 | Maeth et al. | 128/268 |
| 3,339,546 | 9/1967 | Chen | 128/268 X |
| 3,426,754 | 2/1969 | Bierenbaum et al. | 128/268 X |
| 3,464,413 | 9/1969 | Goldfarb et al. | 128/268 |
| 3,512,997 | 5/1970 | Cohly et al. | 128/296 X |
| 3,598,122 | 8/1971 | Zaffaroni | 128/268 |
| 3,598,123 | 8/1971 | Zaffaroni | 128/268 |

*Primary Examiner*—Aldrich F. Medbery
*Attorney, Agent, or Firm*—Thomas E. Ciotti; Paul L. Sabatine; Edward L. Mandell

[57] ABSTRACT

A bandage for continuously administering controlled quantities of systemically active drugs through the skin or mucosa is disclosed. This bandage has a backing member which defines one of its face surfaces and at least one reservoir containing the systemically active drug formulation which defines the other face surface. The reservoir can be a distinct layer of the bandage or can be a plurality of microcapsules distributed throughout a matrix. The material used to form the reservoir is drug release rate controlling and for a prolonged period continuously meters a controlled and predetermined flow of drug from the reservoir to the skin or mucosa of a patient.

21 Claims, 6 Drawing Figures

INVENTOR
ALEJANDRO ZAFFARONI

Edward J Mandell
ATTORNEYS

1

MEDICAL BANDAGE

BACKGROUND OF THE INVENTION

This invention relates to a device for the administration of drug and, more particularly, to a medical bandage for the controlled continuous metering of the flow of systemically active drug to the skin or mucosa over a period of time. "Systemically active" drugs, as that term is used in this specification and the appended claims, are agents which, when applied to the skin or mucosa, are absorbed through the body surface to which applied and are transported from their site of application by the recipient's circulatory system or lymphatic system, to cause a pharmacologic or physiologic response at a remote site in the body.

Systemically active drugs are conventionally administered either orally or by injection, with the primary objective of the mode being to achieve a given desired blood level of drug in circulation over a period of time. However, these prior art methods possess certain shortcomings resulting in the failure to obtain these goals. For example, the oral route is inadequate for several reasons even though the drug is administered at periodic intervals according to a well defined schedule. The rate of absorption of drug through the gastrointestinal tract is affected by both the contents of the tract and the time of passage of drug through the small intestine. Therefore, such variables as whether the drug is administered before or after eating and the type and quantity of food eaten (for example, high or low fat content), or whether administered before or after a bowel movement, affect the rate of absorption of the drug which takes place in the small intestine. Additionally, the time of passage of drug through the small intestine is affected by the rate of peristaltic contracting, adding further uncertainty. Also important is the rate of circulation of blood to the small intestine and the fact that many drugs administered by this route are rendered inactive by gastric acid and digestive enzymes of the gastrointestinal tract or liver where the drug can be metabolized to an inactive product by that organ. These factors make it difficult to achieve a desired time course of concentration of the drug in the blood. The almost inevitable result of oral administration of drugs through the gastrointestinal tract is that the level of drug in circulation surges to a peak level at the time the drug is administered, followed by a decline in concentration in the blood and body compartments. Thus, a plot of drug in circulation after administration of several tablets a day has the appearance of a series of peaks which may surpass the toxic threshold of the drug, and valleys which fall below the critical point needed to achieve the desired therapeutic effect.

The administration of drugs by injection can entail certain disadvantages. For example, very strict asepsis must be maintained to avoid infection of the blood, the vascular system or heart. Drug administration by poor intravenous injection technique may result in perivascular injection when it is not intended; and the typical result of injection into the blood is a sudden rise in the blood concentration followed by an uncontrolled decline. Additionally, administration of drugs by injection is inconvenient and painful. Other dosage forms for systemic administration of drug, such as rectal suppositories and sublingual lozenges, also produce nonuniform levels of the therapeutic agent in circulation. These dosage forms require great patient cooperation, have low patient acceptability, and are sparingly used throughout most of the world.

To avoid the problems discussed above, it has been suggested that systemically active drugs can be administered through the skin. Uncertainties of administration through the gastrointestinal tract and the inconvenience of administration by injection are eliminated. Since a high concentration of drug never enters the body, problems of pulse entry are overcome. Despite these advantages of administering systemically active drugs through the skin, prior art devices designed for this purpose do not provide continuous administration and delivery rate.

SUMMARY OF THE INVENTION

Accordingly, an object of this invention is to provide a device for the administration of systemically active drugs which overcomes the aforesaid disadvantages inherent in prior art modes of administration.

Another object of this invention is to provide a reliable and easily applied device for continuously administering controlled quantities of systemically active drugs through the skin or mucosa.

A further object of this invention is to provide a complete dosage regime for a particular time period, the use of which requires a patient intervention only for initiation and termination.

In accomplishing these objects, one aspect of the invention resides in a bandage for use in the continuous administration of systemically active drugs by absorption thru the skin or mucosa of a patient. The bandage comprises a laminate of (1) a backing member defining one face surface of the bandage, and, defining the other face surface of the bandage, (2) at least one reservoir comprised of a systemically active drug formulation confined within a wall member which is formed from drug release rate controlling material to continuously meter the flow of a therapeutically effective amount of drug from the reservoir to the skin or mucosa at a controlled and predetermined rate over a prolonged period of time and (3) means to secure the bandage to the patient.

Another aspect of this invention resides in a bandage comprised of a laminate of: (1) a backing member defining one face surface of a bandage; (2) a discrete middle reservoir containing a drug confined therein, the reservoir being formed of material permeable to passage of the drug; and wherein one or more drug release rate controlling membranes are laminated to the surface of the reservoir defining the other face surface of the bandage so as to continuously meter the flow of a therapeutically effective amount of the drug from the reservoir to the skin or mucosa of a patient at a controlled and predetermined rate over a period of time. The reservoir can be a container having the agent confined therein or a solid or microporous matrix having agent dispersed therein. Means are also provided for attaching the bandage to the desired area of the patient's body.

Still another embodiment of this invention resides in a bandage comprised of a backing member bearing a non-adhesive matrix layer on one surface thereof. The matrix has distributed therethrough a plurality of microcapsules acting as an external drug reservoir, each of which microcapsules comprises a systemically active drug confined within a body of drug release rate controlling material to continuously meter the flow of a therapeutically effective amount of drug to the skin or mucosa from the microcapsules at a controlled rate over a period of time. Means are also provided for attaching the bandage to the desired area of the patient's body.

Other objects, features and advantages of the invention will be apparent to those skilled in the art from the detailed description of the invention which follows, and from the drawings.

Figure 2:
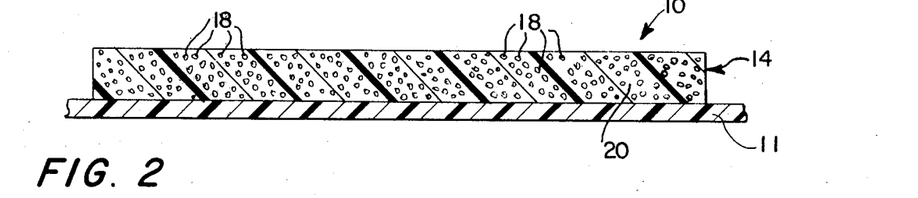
FIG. 2 is a cross-sectional view of the bandage illustrated in FIG. 1, taken along the line 2—2'.
Figure 3:
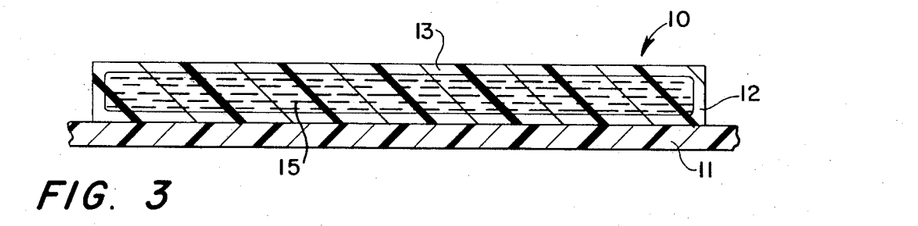
FIG. 3 is a cross-sectional view of another bandage of the invention.
Figure 3A:
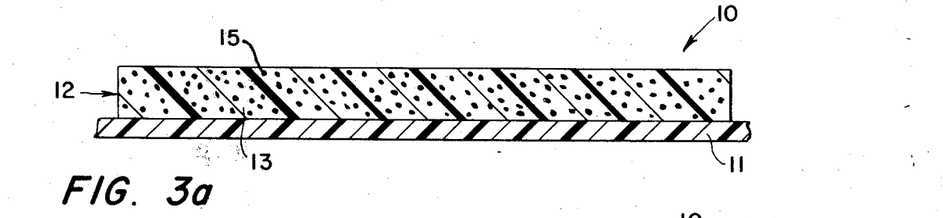
FIG. 3a is a cross-sectional view of yet another bandage of the invention.
Figure 4:
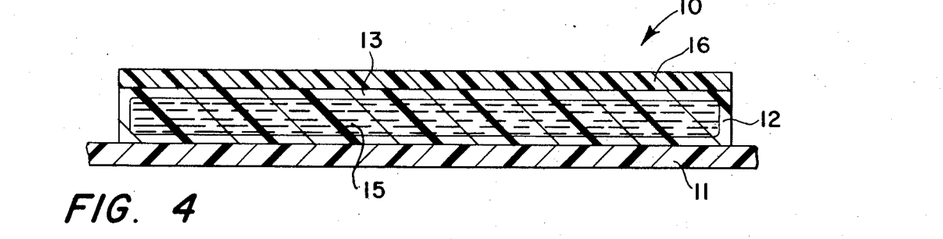
FIG. 4 is a cross-sectional view of a modified bandage of the invention including a rate controlling membrane serving as the face surface of the bandage.

The term "reservoir" as used herein to define the drug-containing portion of the subject bandages is intended to connote a broad class of structures capable of fulfilling the intended function and includes both discrete microcapsules (FIGS. 1 and 2) as well as distinct reservoir compartments or layers (FIGS. 3, 3a and 4). Likewise, as will be hereinafter more completely developed, the foregoing term encompasses walled containers (FIG. 3) having one or more interior drug-containing chambers as well as solid matrices (FIG. 3a) or microporous matrices (not shown) having a systemically active drug distributed therethrough. Furthermore, the terms "wall" and "wall member" as used herein are intended to define the material confining the drug and including distinct wall members, such as 13, the encapsulating material for the microcapsules 18 as well as non-adhesive matrix material 20 itself.

The term "drug release rate controlling material" includes both microporous type materials possessing from 5% to 95% voids and having an effective pore size of from about 50 angstroms to about 100 microns and molecular diffusion or solid type materials with pore sizes significantly below 50 angstroms and which materials can be adapted to meter the release of drug by either of the diffusive type mechanisms set forth hereinafter.

DETAILED DESCRIPTION OF THE INVENTION

In accordance with this invention, there is provided a bandage suitable, by virtue of the rate controlling materials employed therein, for the predetermined controlled administration of drug to the skin or mucosa of the body over a period of time. To use the bandage of the invention, it is applied to the patient's skin or mucosa and should be in firm contact therewith so as to form a tight seal. Flow of drug from the reservoir is metered through the rate release controlling material in accordance with the laws of diffusion, as hereinafter discussed, at a predetermined rate. In operation, drug molecules are continuously removed from the reservoir and migrate to the skin or mucosa of the patient where the drugs are absorbed and enter circulation through the capillary network.

The reservoir containing the drug is formed of material permeable to the drug to permit passage of the drug. Depending upon the particular embodiment, the drug reservoir can be of drug rate release controlling material or otherwise. However, as is apparent in the latter case, the drug must first pass through microporous or molecular diffusion rate release controlling material prior to reaching the skin or mucosa. It is therefore critical to the practice of this invention for all embodiments that, at some point after or concurrent with the release of drug from the reservoir and prior to reaching the skin or mucosa, the drug pass through the drug release rate controlling membrane or matrix material to meter the flow thereof. The rate of passage or permeation of drug through the rate controlling material is determined by the transfer mechanism which can be either by:

1. diffusive flux of drug molecules as is the case, as hereinafter described, where the rate controlling membrane or matrix material is of a microporous nature and is impregnated with a diffusive medium for the drug in which the drug molecules can dissolve in and flow through to a direction of lower chemical potential. The rate controlling material when of a microporous nature has a structure that enables the drug to pass through the pre-existing pores or capillaries, by diffusive permeability.

2. diffusive flux of drug molecules as is the case where the rate controlling membrane or matrix material is of a solid nature in which the drug molecules can dissolve in and flow through to a direction of lower chemical potential.

For drug transfer mechanisms (1) or (2) set forth above, the release rate can be controlled in accordance with Fick's First Law, depending on the particular design by selection of dependent variables such as the diffusivity and solubility of the drug in the diffusive medium, thickness of the rate controlling material and in the case of microporous materials additionally by the porosity of the material.

Therefore, the selection of appropriate materials for fabricating the rate controlling membrane or matrix materials will be dependent on the particular drug to be used in the bandage. Both organic and inorganic polymeric materials can be shaped into a wide variety of forms with tailored morphology and a wide range of chemical and physical properties to advantageously control release of a wide variety of drugs, including those with large molecular structures such as insulin, and over a large dosage range by appropriate selection. Additionally, in the case wherein microporous materials are employed, by impregnating the interconnected pores of the microporous structure with a diffusive medium for the drug to be administered, a given microporous membrane or matrix material can be adapted to control the release of drugs having a wide range of chemical properties by diffusive permeability. Thus, by varying the composition, pore size, and effective thickness of the microporous rate controlliing material, the viscosity of the drug to be administered by appropriate formulation or by impregnating the material with suitable solvent, the dosage rate per area of bandage can be controlled since the material functions to meter the flow of drug from the device. Therefore, bandages of the same surface area can provide different dosages of a drug by varying the above discussed parameters. The rate controlling materials of this invention are known in the art. The rate controlling structures formed from the materials can be isotropic, wherein the structure is homogenous throughout the cross-section of the matrix or membrane material, or anisotropic wherein the structure is non-homogenous. These rate controlling structures are commercially available and when microporous in nature can be made by a multitude of different methods, e.g. etched nuclear track, and materials employed, e.g. polyelectrolyte, ion exchange polymers, as described in R. E. Kesting, *Synthetic Polymer Membranes*, McGraw Hill, Chapters 4 and 5, 1971; J. D. Ferry, "Ultrafiltration Membranes", *Chemical Review*, Vol. 18, page 373, 1934. In order to obtain the most advantageous results, the materials should be formed into structures with the desired morphology in accordance with methods known to those skilled in the art to achieve the desired release rate of drug. Additionally, the material must have the appropriate chemical resistance to the drug used and be non-toxic when used as an element of the bandage of the invention.

Materials useful in forming the rate controlling matrix and membrane materials used in this invention when microporous in nature include, but are not limited to the following.

Polycarbonates, i.e. linear polyesters of carbonic acids in which carbonate groups recur in the polymer chain, by phosgenation of a dihydroxy aromatic such as bisphenol A. Such materials are sold under the trade designation Lexan by the General Electric Company.

Polyvinylchlorides; one such material is sold under the trade designation Geon 121 by B. F. Goodrich Chemical Company.

Polyamides such as polyhexamethylene adipamide and other such polyamides popularly known as "nylon". One particularly advantageous material is that sold under the trade name "NOMEX" by E. I. DuPont de Nemours & Co.

Modacrylic copolymers, such as that sold under the trade designation DYNEL and formed of polyvinylchloride (60%) and acrylonitrile (40%), styrene-acrylic acid copolymers, and the like.

Polysulfones such as those of the type characterized by diphenylene sulfone groups in the linear chain thereof are useful. Such materials are available from Union Carbide Corporation under the trade designation P-1700.

Halogenated polymers such as polyvinylidene fluoride sold under the trade designation Kynar by Pennsalt Chemical Corporation, polyvinylfluoride sold under the trade name Tedlar by E. I. DuPont de Nemours & Co., and the polyfluorohalocarbon sold under the trade name Aclar by Allied Chemical Corporation.

Polychloroethers such as that sold under the trade name Penton by Hercules Incorporated, and other such thermoplastic polyethers.

Acetal polymers such as the polyformaldehyde sold under the trade name DELRIN by E. I. DuPont de Nemours & Co., and the like.

Acrylic resins such as polyacrylonitrile polymethyl methacrylate, poly n-butyl methacrylate and the like.

Other polymers such as polyurethanes, polyimides, polybenzimidazoles, polyvinyl acetate, aromatic and aliphatic, polyethers, cellulose esters, e.g. cellulose triacetate; cellulose; collodion (cellulose nitrate with 11% nitrogen); epoxy resins; olefins, e.g. polyethylene polypropylene; porous rubber; cross-linked poly(ethylene oxide); cross-linked polyvinylpyrrolidone; cross-linked poly(vinyl alcohol); polyelectrolyte structures formed of two ionically associated polymers of the type as set forth in U.S. Pat. Nos. 3,549,016 and 3,546,142; derivatives of polystyrene such as poly(sodium styrenesulfonate) and polyvinylbenzyltrimethyl-ammonium chloride); poly(hydroxyethyl methacrylate); poly(isobutyl vinyl ether), and the like, may also be utilized. A large number of copolymers which can be formed by reacting various proportions of monomers from the aforesaid list of polymers are also useful.

Preferred materials useful in forming the rate controlling matrix and membrane used in this invention when of the solid type, i.e. pore structure less then 50 angstroms, are the organopolysiloxane rubbers, commonly known as silicone rubbers. Suitable silicone rubbers are the conventional heartcurable silicone rubbers and the room temperature vulcanizable silicone rubbers.

Conventional silicone rubbers which are converted to the rubbery state by the action of heat are predominantly linear organopolysiloxanes having an average degree of substitution of about two organic groups attached directly to silicon per silicon atom. Preferably, the organic groups are monovalent hydrocarbon radicals such as alkyl, aryl, alkenyl, alkaryl, aralkyl, and the of these, the methyl, phenyl and vinyl radicals are most preferred. Variation of the organic groups in the silicone rubber can be used to vary the solubility of the drug in the polymer and hence can control the speed of migration of the drug through the polymer. Also, drugs which are insoluble in one type of silicone rubber may be soluble in a different type of polymer. One especially preferred class of silicone polymers are the pure dimethylpolysiloxanes. Room temperature vulcanizable silicone rubbers are also commercially available and are known to the art. In general, they employ the same silicone polymers as discussed above although the polymers often contain a greater amount of silicon bonded hydroxy groups. This type of silicone rubber will cure at room temperature in the presence of an appropriate catalyst, such as stannous 2-ethylhexoate. Exemplary patents disclosing the preparation of silicone rubbers are U.S. Pat. Nos. 2,541,137; 2,723,966; 2,863,846; 2,890,188; 2,927,907; 3,002,951 and 3,035,016.

Another class of materials suitable for use in forming the rate structures are the hydrophilic polymers of monoesters of an olefinic acid, such as acrylic acid and methacrylic acid. Exemplary polymers of this class include poly(hydroxyethylacrylate) and poly(hydroxyethylmethacrylate). These polymers are commerically available and their preparation is described in U.S. Pat. Nos. 2,976,576 and 3,220,960, as well as in Belgian Pat. No. 701,813. When using these hydrophilic polymers, the drug is normally dissolved in a solvent such as a lower alcohol to promote passage of the drug through the polymer.

Other exemplary materials for use in forming the rate structures in this invention include polyvinylalcohol, polyvinylacetate, plasticized polyvinylchloride, plasticized nylon, collagen, modified collagen, gelatin, and waxes such as polyethylene wax, oxidized polyethylene wax, hydrogenated castor oil, etc. In addition, most of the materials suitable for forming the rate controlling materials when microporous can be used for forming the rate controlling material of a solid nature.

Figure 1:
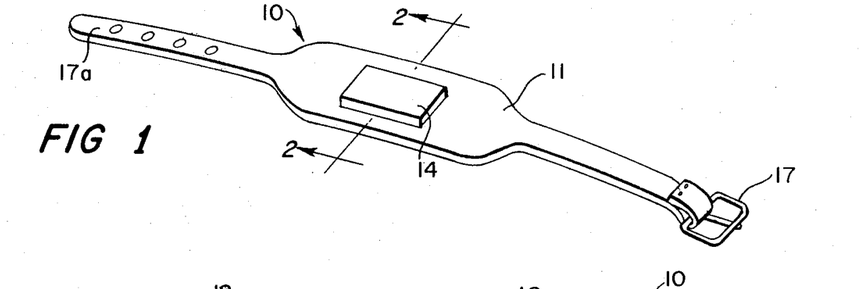
FIG. 1 is a perspective view of one bandage of the invention.

As illustrated in FIGS. 1 and 2, bandage 10 of this invention is comprised of a backing member 11 bearing a drug layer 14 on one surface thereof. Layer 14 comprises a non-adhesive matrix 20 having microcapsules 18 (not shown in FIG. 1) of a systemically active drug encapsulated with a material permeable to passage of the drug uniformly distributed therethrough. In FIG. 1, there is also depicted means integral with the said backing member 11, and terminating at either end in buckle 17 and buckle strap 17a, for attaching the bandage to the body of the patient.

As illustrated in FIG. 3, an alternative design of bandage 10 in accordance with this invention comprises a backing member 11 having a reservoir 12 on one surface thereof. Reservoir 12 contains a systemically active drug 15 and at least wall 13 of reservoir 12 is permeable to passage of the drug.

FIG. 3a illustrates an alternative design of the bandage shown in FIG. 3, in which the bandage 10 also comprises a backing member 11 having a reservoir 12 on one surface thereof. But in this embodiment, the reservoir 12 contains the systemically active drug 15 uniformly distributed throughout non-adhesive wall member or matrix 13 formed of drug release rate controlling material.

FIG 4 illustrates a modified form of the bandage shown in FIG. 3, in which a rate controlling membrane 16 is laminated to the face of wall 13.

Figure 5:
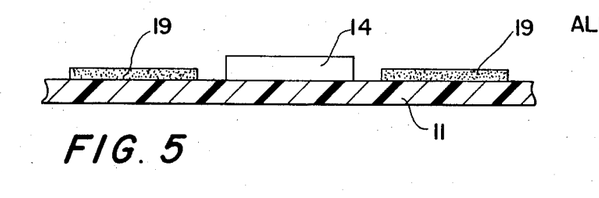
FIG. 5 is a cross-sectional view of another bandage of the invention particularly adapted for application to the oral mucosa.

FIG. 5 illustrates another alternative design of the bandage of this invention wherein the means to attach the bandage to the patient comprises adhesive 19 located adjacent to the drug layer 14.

In the embodiment illustrated in FIGS. 1 and 2, microcapsules constitute the drug reservoir. To provide the microcapsules, the encapsulating material can be uniformly impregnated with the drug or drug solution to form microcapsules which are a matrix, porous or solid, having the drug distributed therethrough. Alternatively, particles or solutions of drugs can be encapsulated with thin coatings of the encapsulating material to form microcapsules having an interior chamber containing the drug. If desired, particles of a matrix, such as starch, gum acacia, gum tragacanth, and polyvinylchloride, can be impregnated with the drug and encapsulated with another material such as the rate controlling materials previously discussed which function as a solubility membrane to meter the flow of drug to the non-adhesive matrix 20; use of a matrix and a different solubility membrane can slow the passage of the drug from the microcapsules which is desirable with drugs that are released too rapidly from available encapsulating materials. In contrast, by encapsulating a solution of the drug, the solvent speeds passage of the drug through the microcapsule walls.

Any of the encapsulation or impregnation techniques known in the art can be used to prepare the microcapsules to be incorporated into the bandage in accord with this invention. Thus, the drug or drug solution can be added to the encapsulating material in liquid form and uniformly distributed therethrough by mixing; or solid encapsulating material can be impregnated with the drug by immersion in a bath of the drug to cause the drug to diffuse into the material. Subsequently, the solid material can be reduced to fine microcapsules by grinding, each of the microcapsules comprising drug coated with and distributed throughout the encapsulating material. Alternatively, fine particles or solutions of the drug can be encapsulated with a coating. One suitable technique comprises suspending dry particles of the drug in an air stream and contacting that stream with a stream containing the encapsulating material to coat the drug particles. The microcapsules when porous in nature can be made by methods described in my coincidentally filed application Ser. No. 169,976, entitled "BANDAGE FOR THE ADMINISTRATION OF DRUG BY CONTROLLED METERING THROUGH MICROPOROUS MATERIALS". This application is relied upon and incorporated herein by reference. Usually, the microcapsules have an average particle size of from 1 to 1000 microns, although this is not critical to the invention.

The microcapsules, however made, are then mixed with the non-adhesive matrix. This mixture is then coated onto a backing member, usually to provide a layer 0.01 to 7 millimeters thick, although these limits can be exceeded if more or less drug is required. The purpose of the backing is to provide support for the bandage and to prevent passage of the drug away from the body surface to which the bandage is applied.

Choices of materials for forming the non-adhesive matrix 20 are governed in large part by the drug to be incorporated in the particular bandage, as well as by the desired rate of release of the drug. Preferably, a matrix material is selected which has a drug release rate which is greater than the drug release rate of the material encapsulating the systemically active drug such that the latter is the rate controlling step. Therefore, in this case, the matrix does not serve as a rate-controlling barrier to the drug and the desired release rate is obtained based on the selection of encapsulating material. It has been found desirable to employ a matrix material which has a drug permeability at least twice and more preferably up to 100-fold that of the encapsulating material for the particular dispersed drug. It should be understood that it is also within the purview of this invention to employ a matrix material which possesses a drug release rate which is slower than the encapsulating material, in which case the rate of drug release is determined by the selection of matrix material. Exemplary matrix materials are those polymeric materials set forth above as suitable for forming the rate controlling materials with the provision that the actual selection made in any given instance be made with regard to the permeability of the encapsulating materials in relation to the considerations described above.

In the embodiment employing a distinct reservoir layer, e.g., FIG. 3, the reservoir can be formed by molding into the form of a hollow container with the drug trapped therein. Alternatively, the reservoir can be in the form of an envelope formed from sheets of polymeric material permeable to passage of the drug and enclosing the drug. While the walls of the reservoir can be of any convenient thickness, usually they have a thickness of from 0.01 to 7 millimeters. In a further embodiment, see FIG. 3a, the reservoir can comprise a solid or microporous matrix having the drug uniformly distributed therethrough. This can be accomplished by adding the drug to the matrix material in liquid form and subsequently converting the matrix to a solid by curing or cooling; or by immersing the solid matrix in the drug to effect diffusion of the drug into the matrix. Thus, the reservoir of the bandage of this invention is a hollow drug container or a solid or gel matrix. Drug is metered through the reservoir wall to the skin with the rate controlled by the composition and thickness of the reservoir wall.

Selection of appropriate materials for fabricating the reservoir wall will be dependent on the particular drug to be used in the bandage. By varying the composition and thickness of the reservoir wall, the dosage rate per area of bandage can be controlled, for the reservoir wall acts as a rate controlling membrane to meter the flow or diffusion of drug from the reservoir to the skin. Thus, bandages of the same surface area can provide different dosages of a drug by varying the characteristics of the reservoir wall. While it is only necessary that the wall of the reservoir in contact with the patient be permeable to the drug, for convenience, all of the walls of the reservoir normally are formed of the same material. Materials used to form the reservoir, including the microcapsules, are those capable of forming film walls or matrices through which drug can pass at a controlled rate by diffusion. Fabrics, fibrous masses, and the like, which merely absorb and release drug solutions in a gross and uncontrollable manner, are unsuitable since predictable drug release cannot be obtained.

One surface of the drug reservoir bears a backing member. The purpose of the backing is to prevent passage of the drug through the surface of the reservoir distant from the patient's skin or mucosa. An ancillary purpose of the backing is to provide support for the bandage, and to supply means for attaching the bandage to the desired situs on the patient. When the outer surface of the reservoir is impermeable to the drug and strong enough, the backing becomes unnecessary, or, stated differently, can be considered to be integral with the said reservoir. It will be apparent to those skilled in the art that many and varied means may be employed for securing the bandage of this invention onto the patient at the desired location. The strap and buckle illustrated in FIG. 1 is merely one of many ways to secure the bandage. Since the buckle is adjustable, this means is convenient both for patient comfort and ease of operation. Simple tie strings or straps, one at each end of the bandage, may also be employed for this purpose. Besides a metal or plastic buckle and strap, there may also be employed plastic or fabric fasteners of the Velcro type described in U.S. Pat. Nos. 2,717,437; 3,009,235; 3,083,737; and 3,154,837. These fasteners consist essentially of two pieces of fabric, such as nylon tape, one of which is covered with a myriad of finely woven filaments formed into permanent hooks and the other of which is covered with soft loops. When pressed together the two ends form a shear resistant band. However, they are easily separated by simply peeling them apart. Alternatively, the backing material may be composed of a material which is self-adhering, such as a silicone elastomer, in cases it is impermeable to the drug used, and the bandage wrapped around, e.g., the patient's arm, with the ends overlapping, resulting in a secure fit on the patient.

In a modified embodiment, as depicted in FIG. 4, the passage of the drug from the reservoir to the skin or mucosa is controlled by adding one or more rate controlling membranes. Drug 24 is confined in the polymeric matrix material which acts as the reservoir for the drug. Matrix material can be solid material as illustrated, or microporous. If desired, additional membranes can be juxtaposed in order to achieve optimum rate release properties. The matrix material when solid or microporous should have a release rate to drug which is higher than that of the rate controlling membrane, such that passage through the latter is the rate controlling step. Any of the materials previously mentioned for use in fabricating the rate controlling materials may be used for the membranes. Of course, in each instance, the membrane will have different characteristics than the reservoir wall of the particular device. This use of a pair of membranes, that is, the reservoir wall and the further solubility membrane, allows for precise control of drug release; for the thickness and composition of both membranes can be varied to provide for a wide range of dosage levels per a given area of bandage.

FIG. 5 illustrates an alternative means for securing the bandage to the patient, i.e., with the use of an adhesive layer located on the backing, next to, or surrounding the drug reservoir. Such a modification of the bandage of this invention results in a bandage which closely resembles a common household bandage normally used for covering small lacerations and abrasions. The use of the adhesive securing means is, as above noted, particularly adapted for application of the bandage to the oral mucosa.

It will also be evident that the bandage may be applied to the skin of the patient and secured thereon by wrapping the bandage with a separate securing means, e.g., an elastic tape having its loose end secured to itself by means of common metal fasteners.

As above discussed, the rate controlling materials when microporous in nature can be adapted to control the release of drug by diffusive permeation wherein the micropores are impregnated or otherwise filled with a diffusive medium for the drug to be administered. The material can be impregnated with the diffusive medium by methods well known to the art, e.g. as by immersion in a bath of the material to permit the diffusive medium material to fully saturate the micropores. The impregnation technique can be employed with any of the embodiments represented herein. In cases where the microporous rate controlling materials employed are water permeable, body fluids will self-migrate into the microporous material after the bandage has been in contact with the skin for a suitable period of time to provide the diffusive medium, as hereinafter described, without the necessity of carrying out a separate impregnation step. Additionally, the pores can be self-filled by migration of the diffusive medium by contact with the composition employed to prepare the drug formulation, as later described.

The diffusive medium is one which enables the drug to dissolve therein and flow by diffusion at the desired rate. It can be either of a liquid or solid nature and be a poor or good solvent for the drug. A medium with poor solvent properties for the drug is desired when the required release rate is low and of course the converse is true when the desired release rate is high.

The art provides many useful approaches to enable selection of particular solvent-drug systems. Specific attention is called to *Remington's Pharmaceutical Sciences*, Chapters 19 and 71. The solvent selected must be non-toxic and one in which the rate controlling microporous material has the required solubility. The materials which are useful for impregnating the micropores can be polar, semi-polar or non-polar. Exemplary are any of the pharmaceutically acceptable solvents such as water, alcohols containing 2 to 10 carbon atoms, such as hexanol, cyclohexanol, benzylalcohol, 1,2-butanediol, glycerol, and amyl alcohol; hydrocarbons having 5 to 12 carbon atoms such as n-hexane, cyclohexane, and ethyl benzene; aldehydes and ketones having 4 to 10 carbon atoms such as heptyl aldehyde, cyclohexanone, and benzaldehyde; esters having 4 to 10 carbon atoms such as amyl acetate and benzyl propionate; etheral oils such as oil of eucalyptus, oil of rue, cumin oil, limonene, thymol, and 1-pinene; halogenated hydrocarbons having 2 to 8 carbon atoms such as n-hexyl chloride, n-hexyl bromide, and cyclohexyl chloride; or mixtures of any of the foregoing materials. Also suitable are many of the conventional non-toxic plasticizers used in the fabrication of microporous rate controlling material, e.g. octyl diphenyl phosphate. When these plasticizers are suitable diffusive materials for the drug used, advantageously, the necessity for filling the pores by a separate step is thus obviated. Other plasticizers known to the art can be employed, such as long-chain fatty amides, higher alcohols, and high boiling esters such as di(isooctyl) sebacate or di(2-ethyl hexyl) phthalate.

In practicing this invention one can employ any systemically active drug which will be absorbed by the body surface to which the bandage is applied, consistent with their known dosages and uses. Of course, the amount of drug necessary to obtain the desired therapeutic effect will vary depending on the particular drug used. Suitable systemic drugs include, without limitation, Anti-microbial Agents such as penicillin, tetracycline, oxytetracycline, chlortetracycline, chloramphenicol, and sulfonamides; Sedatives and Hypnotics such as pentabarbital sodium, phenobarbital, secobarbital sodium, codeine, ($\alpha$-bromoisovaleryl) urea, carbromal, and sodium phenobarbital; Psychic Energizers such as 3-(2-aminopropyl) indole acetate and 3-(2-aminobutyl) indole acetate; Tranquilizers such as reserpine, chlorpromazine hydrochloride, and thiopropazate hydrochloride; Hormones such as adrenocorticosteroids, for example, 6$\alpha$-methylprednisolone; androgenic steroids, for example, methyltestosterone, and fluoxymesterone; estrogenic steroids, for example, estrone, 17$\beta$-estradiol and ethinyl estradiol; progestational steroids, for example, 17$\alpha$-hydroxyprogesterone acetate, medroxyprogesterone acetate, 19-norprogesterone, and norethindrone; and thyroxine; Antipyretics such as aspirin, salicylamide, and sodium salicylate; morphine and other narcotic analgesics; Antidiabetics, e.g. insulin; Cardiovascular Agents, e.g. nitroglycerin, and cardiac glycosides such as digitoxin, digoxin, ouabain; Antispasmodics such as atropine, methscopolamine bromide, methscopolamine bromide with phenobarbital; Antimalarials such as the 4-ammoquinolines, 9-aminoquinolines, and pyrimethamine; and Nutritional Agents such as vitamins, essential amino acids, and essential fats.

In addition to the aforementioned drugs, simple pharmacologically acceptable derivatives of the drugs, such as ethers, esters, amides, acetals, salts, etc. or formulations of these drugs, having the desired polymeric permeability or transport properties can be prepared and used in practicing the invention. Drugs mentioned above can be used alone or in combination with others and each other. Of course, the derivatives should be such as to convert to the active drugs within the body through the action of body enzyme assisted transformations, pH, etc.

The above drugs and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of caster oil; liquid glyceryl triester of a lower molecular weight fatty acid; lower alkanols; oils such as corn oil; peanut oil, sesame oil and the like, with emulsifiers such as mono-or di-glyceride of a fatty acid, or a phosphatide, e.g. lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispensing agents such as lecithin; polyoxyethylene stearate; and the like. The carrier may also contain adjuvants such as preserving, stabilizing, wetting, emulsifying agents, and the like.

The drug can also be mixed in the reservoir with a transporting agent, that is, a material that aids or assists the drug delivery device to achieve the administration of a drug to a drug receptor, for example, by enhancing penetration through the skin. The transporting aids suitable for the purpose of the invention are the therapeutically acceptable transporting aids that do not adversely affect the host, the drug, or alter or adversely affect the materials forming the drug delivery device. The transporting aids can be used alone or they can be admixed with acceptable carriers and the like. Exemplary of transporting aids include manovalent, saturated and unsaturated aliphatic cycloaliphatic and aromatic alcohols having 4 to 12 carbon atoms, such as hexanol, cyclohexane and the like; aliphatic cycloaliphatic and aromatic hydrocarbons having from 5 to 12 carbon atoms such as hexane, cyclohexane, isopropylbenzene and the like; cycloaliphatic and aromatic aldehydes and ketones having from 4 to 10 carbon atoms such as cyclohexanone; acetamide; N,N-di(lower) alkyl acetamides such as N,N-diethyl acetamide, N,N-dimethyl acetamide, N-(2-hydroxyethyl)acetamide, and the like; and other transporting agents such as aliphatic, cycloaliphatic and aromatic esters; N,N-di-lower alkyl sulfoxides; essential oils; halogenated or nitrated aliphatic, cycloaliphatic and aromatic hydrocarbons; salicylates; polyalkylene glycol silicates; mixtures thereof; and the like.

The amount of active agent to be incorporated in the bandage to obtain the desired therapeutic effect will vary depending upon the desired dosage, the permeability of the rate controlling materials of the bandage which are employed to the particular agent to be used, and the length of time the bandage is to remain on the skin or body mucosa. Since the bandage of this invention is designed to control drug administration for an extended period of time, such as 1 day or more, there is no critical upper limit on the amount of agent incorporated into the bandage. The lower limit is determined by the fact that sufficient amounts of the agent must remain in the bandage to maintain the desired dosage. In order to achieve a therapeutic effect in a human adult, the daily release dosage of atropine should be in the range of between 200 and 600 micrograms per day. Thus, for example, using atropine and with a bandage intended to remain in place for 1 week, and with a release rate of 500 micrograms of atropine per day, at least 3.5 mg of atropine would be incorporated in the bandage. Generally, the drug delivery bandages made according to the invention can release at a controlled rate about 25 n nograms to about 1 gram of drug or larger amounts per day. Of course, other devices for use for different time periods such as week or month are also readily made by the invention.

The effective rate of release of the active agent to the skin or mucosa can be in the range of from 0.5 to 1000 micrograms per square centimeter of bandage per day. The exact amount will depend on the desired dosage as well as the condition to be treated. The desired effective rate of release of active agent can be obtained by altering the earlier discussed parameters affecting the release rate controlling barrier. In the case of the microencapsulated active agent, the release rate can also be controlled by varying the number of microcapsules present in a given volume of the matrix of the device. This is a particularly desirable feature of this aspect of the invention. Additionally, the duration of action of the device can be altered by controlling the amount of active agent initially incorporated consistent with the release rate. Further, the release rate of drug, as well as the duration of release of the drug from the device, can be predetermined to be in consonance with the optimum therapeutic values. Once this dosage level in micrograms per square centimeter of bandage has been determined, the total amount of drug to be incorporated in the bandage can be established by obtaining the release rate of the agent in the particular material or materials which are to be used. Those skilled in the art can readily determine the rate of permeation of agent through the rate controlling material or selected combinations of rate controlling materials. Standard techniques are described in *Encyl. Polymer Science and Technology*, Vols 5 and 9, pages 65 to 85 and 795 to 807, 1968; and the references cited therein.

The required surface area of the drug reservoir will depend on the activity of the drug and the rate of its absorption through the skin. Usually, the reservoir's face of the bandage a surface area of 0.5 to 400 squire centimeters, although smaller or larger area bandages can be used.

Various occlusive and non-occlusive, flexible or non-flexible backing members can be used in the adhesive bandage of the invention. Suitable backings include cellophane, cellulose acetate, ethylcellulose, plasticized vinylacetate-vinylchloride copolymers, polyethylene terephthalate, nylon, polyethylene, polypropylene, polyvinylidenechloride, paper, cloth, and aluminum foil. Preferably, a flexible occlusive backing is employed to conform to the shape of the body member.

To prevent passage of the drug away from the exposed surface of the bandage prior to use, the surface generally is covered with a protective release film or foil such as waxed paper. Alternatively, the exposed rear surface of the backing member can be coated with a low-adhesion backsize and the bandage rolled about itself. To enhance stability of the active compounds, the therapeutic bandage usually is packaged between hermetically sealed polyethylene terephthalate films under an inert atmosphere, such as gaseous nitrogen.

To use the bandage 10 of the invention, it is applied to the patient's skin. Drug layer 14, reservoir 12 or membrane 16 should be in firm contact with the skin, preferably forming a tight seal therewith. Drug within microcapsules 18 or reservoir layer 12, whether in solid form or solution, migrates through the walls of the microcapsules or the reservoir layer, acting as a solubility membrane, and to the skin, as by diffusion. Ordinarily, one would expect the drug migration to cease when sufficient drug has reached the outer surface of microcapsules 18 or reservoir layer 12 to create an equilibrium or when matrices 20 and 13 have become saturated with the drug. However, when drug layer 14 is in contact with the patient's skin, drug molecules which are continuously removed from the outer surface of microcapsules 18 migrate through the matrix 20 to the outer surface of the bandage and are absorbed by the skin. Likewise with respect to the reservoir layer 12. Absorbed drug molecules pass through the skin and enter circulation through the capillarly network. While the bandage may be applied to any area of the patient's skin, the lower back and buttocks are the areas of choice. Also, the bandage can be applied to the mucosa of the mouth, for example, by application of the bandage illustrated in FIG. 5 to the palate or the buccal mucosa, to obtain absorption of the drug by the oral mucosa. Although obtaining a liquid tight seal between the skin and bandage is important, it becomes critical in the mouth, and for this reason, adhesive tabs 19 are employed for such application. Without such a seal, irrigation of the oral mucosa by saliva will transfer the drug to the gastrointestinal tract, rather than to circulation through the oral mucosa. In addition, the bandage of the invention can be used to administer drugs to other mucosa of the body, for example, it can be applied to the vaginal mucosa, rectal mucosa, etc. By use of this invention, one ensures that an accurately measured quantity of the active drug is available to the site of application.

Those skilled in the art will appreciate that the bandage of this invention significantly differs from prior art wound dressings or bandages containing antiseptics or topically active drugs. The bandage of this invention contains a systemically active drug encapsulated within a reservoir and is applied to unbroken skin, to introduce the drug to circulation in the blood stream and produce a pharmacologic response at a site remote from the point of application of the bandage. Thus, the bandage functions as an external drug reservoir and provides a complete dosage regime particular time period.

The following examples are merely illustrative to the present invention and should not be construed as limiting the scope of the invention in any way, as these examples and other equivalents thereof will become apparent to those versed in the art in light of the present disclosure, drawings and accompanying claims.

EXAMPLE 1

100 grams of 2-hydroxyethyl methacrylate is mixed with 100 grams of water and tertiary butyl peroxide (0.2 grams) is added. Ethylene glycol dimethacrylate (0.2 grams) is added to the mixture and is heated to 70° C. The resultant, friable, polymeric foam is dried and ground to a powder to obtain average particle size of about 20 micron.

A 10 gram portion of the polymeric powder is mixed with 1 gram glyceryl trinitrate dissolved in ethyl alcohol and the resultant mixture placed on a mechanical roller until the polymeric powder has absorbed the glyceryl trinitrate to saturation. The solution is then filtered.

The resulting microcapsules of glyceryl trinitrate are mixed with 100 grams of liquid dimethyl silicone rubber (Dow-Corning Silastic) to uniformly distribute the microcapsules throughout the solution. The resulting mixture is cured at room temperature, with the addition of 0.5 grams of stannous octoate catalyst, in a mold measuring 5 cm × 5 cm × 5 mm. The cured product is removed from the mold and laminated by the application of heat to the center of a cellulose acetate backing member measuring 2 inches × 4 inches and having connecting straps at both ends, one of which contains an adjustable buckle and suitable for going around the arm.

When applied to the skin of a subject the resulting bandage is effective to administer nitroglycerin through the skin to circulation to provide a continuous administration of the daily dose of nitroglycerin for coronary vasodilation. If desired, the amount of the nitroglycerin to be administered may be increased or decreased by merely varying the size of the above described bandage for application to the skin.

EXAMPLE 2

Dry crystalline powdered megesterol acetate (0.3 gram) is mixed with 25 parts by weight of polydimethylsiloxane, 5 parts by weight of silicone oil and 0.25 parts by weight of stannous octoate catalyst. The ingredients are mixed until a homogenous mixture is produced. The mixture is then cast into a mold and allowed to cure to prepare a matrix having a surface area of 10 square centimeters and 9 mils thick. On one external face surface is placed a microporous membrane of the same external surface area as the matrix. The membrane is sold by Millipore Corporation and designated to the trade as HA, and is characterized by a porosity of 60%, a pore size of 0.45 microns, and a thickness of 4 mils. The above prepared matrix is secured by means of adhesive to a belt suitable for going around the arm of a patient. The belt consists of a band of Teflon, the ends of which have Velcro material. The bandage is effective to control the release of megesterol acetate, and when applied to the female skin, is useful for fertility control.

EXAMPLE 3

3 grams of a polyacrylonitrile fiber sold under the trade designation ORLON by E. I. DuPont de Nemours & Co. was dissolved in 30 grams of an aqueous solution comprising 70% by weight of zinc chloride. After the solution was cooled to about 25° C, 0.250 grams of DIGOXIN was added to the solution. Thereupon, the solution was added dropwise through a No. 21 hypodermic needle into an acetone bath whereupon particles were formed. After being stirred for about 30 minutes in the acetone, the particles were removed and placed in a water bath for 4 hours at room temperature to leach out residual acetone and salt.

The resulting DIGOXIN capsules are mixed with 100 grams of silicone rubber and 0.5 grams of stannous octoate catalyst. The product is molded to a shape of 5 cm × 5 cm × 5 mm and secured to a Mylar belt suitable for going around the arm similar to that prepared in Example 2. The resulting bandage can be used for control of cardiac disorders.

Thus, this invention provides an easy to use device for administering systemically active drugs through the skin or oral mucosa and other body mucosa. Uncertainties of administration through the gastrointestinal tract are avoided and a controlled constant level of drug in circulation can be obtained. Treatment is begun by applying the bandage to the skin or mucosa and terminated by removing it therefrom. The bandage can contain and administer the complete dosage requirements for a particular time period, for example 24 hours. Intervention by the patient is required only to apply and remove the bandage, so that uncertainties through patient error are eliminated.

Although the product of this invention has been referred to as an adhesive bandage, those skilled in the art will appreciate that the term "adhesive bandage" as used herein includes any product having a backing member and a pressure-sensitive adhesive face surface. Such products can be provided in various sizes and configurations, including tapes, bandages, sheets, plasters, and the like.

What is claimed is:
1. A medical bandage for use in the continuous administration to circulation of controlled quantities of systemically active drugs by absorption through the external body skin or mucosa, said bandage being comprised of a laminate of: (1) a backing member defining one face surface of a bandage; bearing (2) a discrete middle reservoir containing a drug confined therein; the reservoir being formed of a material permeable to passage of drug; and wherein one or more drug release rate controlling membranes are laminated to the surface of the reservoir so as to define the other face surface of the bandage to continuously meter the flow of a therapeutically effective amount of drug to the skin or mucosa of the patient at a predetermined rate over a period of time; and (3) means to secure said bandage to the patient.

2. The bandage as defined by claim 1 wherein said reservoir is laminated to said backing member (1).

3. The bandage as defined by claim 2 wherein the reservoir layer is comprised of a walled container having an interior chamber containing the systemically active drug formulation.

4. The bandage as defined by claim 3 wherein only that portion of the walled container which is adapted to be brought contiguous with the skin or mucosa is formed from the drug release rate controlling material.

5. The bandage as defined by claim 2 wherein the reservoir layer is comprised of a matrix of the drug release rate controlling wall material, said matrix having the systemically active drug formulation distributed therethrough.

6. The bandage as defined by claim 2 wherein the wall member comprising the reservoir layer consists of drug release rate controlling material.

7. The bandage as defined by claim 2 wherein one outer surface of the wall member comprising the reservoir layer also defines the said backing member (1).

8. The bandage as defined by claim 1 wherein said reservoir comprises a plurality of discrete microcapsules distributed throughout a matrix.

9. The bandage as defined by claim 8 wherein each of said microcapsules is comprised of systemically active drug formulation microencapsulated with the said drug release rate controlling wall material.

10. The bandage as defined by claim 8 wherein each of said microcapsules is comprised of a matrix of the drug release rate controlling wall material, said matrix having the systemically active drug formulation distributed therethrough.

11. The bandage as defined by claim 8 wherein the ratio of drug release rate from the material forming the microcapsule to the drug release rate from the material forming the matrix is from 1:2 to 1:100.

12. The bandage as defined by claim 8 wherein the body contacting face surface of the bandage has an area of from about 0.5 to 400 square centimeters.

13. The bandage as defined by claim 1 wherein the systemically active formulation is soluble in the drug release rate controlling material.

14. The bandage as defined by claim 1 wherein the drug formulation comprises a pharmacologically acceptable solvent.

15. The bandage as defined by claim 1 wherein said drug release rate controlling material is silicone rubber.

16. The bandage as defined by claim 1 wherein said drug release rate controlling material is a hydrophilic polymer of an ester of an olefinic acid.

17. The bandage as defined by claim 1 wherein the reservoir is a container having the active agent confined therein.

18. The bandage as defined by claim 1 wherein the reservoir is a solid or microporous matrix having the active agent dispersed therein.

19. The bandage as defined by claim 1 wherein the rate controlling material is microporous and is filled with a medium to permit controlled diffusion of the drug from the reservoir.

20. The bandage as defined by claim 1 wherein the rate controlling membrane material is microporous and is filled with a medium to permit controlled diffusion of the drug from the reservoir.

21. The bandage as defined by claim 1 wherein the means to secure the bandage to a patient comprises a pair of straps connected to opposite ends of the bandage.

* * * * *